US011809674B2

(12) United States Patent
Gilboa-Solomon et al.

(10) Patent No.: US 11,809,674 B2
(45) Date of Patent: Nov. 7, 2023

(54) MACHINE LEARNING METHODS FOR MONITORING A USER'S INTERACTION WITH 3D MEDICAL IMAGES

(71) Applicant: International Business Machines Corporation, Armonk, NY (US)

(72) Inventors: Flora Gilboa-Solomon, Haifa (IL); Aviad Zlotnick, Mitzpeh Netofah (IL)

(73) Assignee: International Business Machines Corporation, Armonk, NY (US)

( * ) Notice: Subject to any disclaimer, the term of this patent is extended or adjusted under 35 U.S.C. 154(b) by 553 days.

(21) Appl. No.: 16/942,812

(22) Filed: Jul. 30, 2020

(65) Prior Publication Data

US 2022/0035489 A1 Feb. 3, 2022

(51) Int. Cl.
| | |
|---|---|
| *G06F 3/0481* | (2022.01) |
| *G16H 30/40* | (2018.01) |
| *G06V 10/40* | (2022.01) |
| *G06N 3/088* | (2023.01) |
| *G06F 18/22* | (2023.01) |
| *G06N 3/045* | (2023.01) |

(52) U.S. Cl.
CPC ............ *G06F 3/0481* (2013.01); *G06F 18/22* (2023.01); *G06N 3/045* (2023.01); *G06N 3/088* (2013.01); *G06V 10/40* (2022.01); *G16H 30/40* (2018.01)

(58) Field of Classification Search
CPC .. G06F 3/0481; G06K 9/6215; G06N 3/0454; G06N 3/088; G06V 10/40; G06V 10/82; G16H 30/40; G16H 30/20; G16H 50/20
USPC ....................................................... 715/708
See application file for complete search history.

(56) References Cited

U.S. PATENT DOCUMENTS

| 7,573,439 | B2 * | 8/2009 | Lau | G06F 3/013 |
| | | | | 345/7 |
| 2006/0215894 | A1 * | 9/2006 | Lakare | G16H 30/40 |
| | | | | 382/128 |
| 2008/0130833 | A1 | 6/2008 | Wang | |
| 2009/0086165 | A1 * | 4/2009 | Beymer | A61B 3/113 |
| | | | | 351/210 |
| 2009/0251466 | A1 * | 10/2009 | Cooper | G06T 15/08 |
| | | | | 345/427 |
| 2011/0128352 | A1 * | 6/2011 | Higgins | G06V 20/653 |
| | | | | 348/46 |
| 2011/0206283 | A1 * | 8/2011 | Quarfordt | G06V 40/193 |
| | | | | 382/220 |

(Continued)

*Primary Examiner* — Shahid K Khan
*Assistant Examiner* — Ahamed I Nazar
(74) *Attorney, Agent, or Firm* — G.E. Ehrlich Ltd.

(57) ABSTRACT

There is provided a method for monitoring interaction with 3D medical images, comprising: dividing the 3D image into a sequence of a 2D images, arranging the sequence into slabs each including at least one 2D image, computing, for each respective slab, a minimal amount of viewing time a user is predicted to spend viewing the respective slab, monitoring, while the 3D medical image is presented on a display, an amount of time a user actually spent viewing portions of the 3D medical image corresponding to each of the of slabs, in response to the amount of time spent viewing a certain portion of the 3D medical image being less than the computed minimal amount of viewing time of a certain slab corresponding to the certain portion, generating instructions for implementation by a user interface indicative of the amount of time spent being less than the computed minimal amount of time.

19 Claims, 3 Drawing Sheets

(56) References Cited

U.S. PATENT DOCUMENTS

| | | | |
|---|---|---|---|
| 2018/0214105 A1* | 8/2018 | Anavi | G06T 7/0014 |
| 2021/0174103 A1* | 6/2021 | Schumacher | G08B 21/06 |
| 2021/0341997 A1* | 11/2021 | Invernizzi | G06F 3/0213 |

* cited by examiner

MACHINE LEARNING METHODS FOR MONITORING A USER'S INTERACTION WITH 3D MEDICAL IMAGES

BACKGROUND

The present invention, in some embodiments thereof, relates to analysis of three dimensional (3D) medical images and, more specifically, but not exclusively, to machine learning methods for monitoring a user's interaction with 3D medical images.

3D medical images, for example, CT scans of the chest, MRI of the abdomen, and the like, include large amounts of data. A radiologist spends considerable amount of time analyzing the entire 3D image dataset in an attempt, for example, to identify clinical abnormalities.

SUMMARY

According to a first aspect, a computer implemented method for monitoring a user's interaction with 3D medical images, comprises: receiving a 3D medical image, dividing the 3D medical image into a sequence of a plurality 2D images, arranging the sequence into a plurality of slabs each including at least one 2D image, computing, for each respective slab, a minimal amount of viewing time a user is predicted to spend viewing the respective slab, monitoring, while the 3D medical image is presented on a display, an amount of time a user actually spent viewing portions of the 3D medical image corresponding to each of the plurality of slabs, in response to the amount of time spent viewing a certain portion of the 3D medical image being less than the computed minimal amount of viewing time of a certain slab corresponding to the certain portion, generating instructions for implementation by a user interface indicative of the amount of time spent being less than the computed minimal amount of time.

According to a second aspect, a computer implemented method for monitoring a user's interaction with real time 2D medical images, comprises: in a plurality of iterations: receiving a 2D medical image captured in real time, analyzing the 2D medical image to determine whether the 2D medical image represents an end of a slab including at least one of a previously obtained sequence of 2D images, computing a minimal amount of viewing time a user should spend viewing the slab, monitoring, while the 2D medical image and the previously obtained sequence of 2D images are presented on a display, an amount of time a user actually spent viewing portions of the 2D medical image and the previously obtained sequence of 2D images corresponding to the slab, in response to the amount of time spent actually spent being less than the computed minimal amount of viewing time, presenting instructions on the display to spend additional time viewing additional 2D images captured from an anatomical region of a subject corresponding to the slab.

In a further implementation form of the first aspect, arranging comprises: computing a similarity dataset indicative of an amount of similarity between each pair of the plurality of 2D images, segmenting the similarity dataset into a plurality of groups by minimizing the amount of similarity between consecutive groups and maximizing the amount of similarity within each group, wherein the plurality of slabs correspond to the plurality of groups.

In a further implementation form of the first aspect, the similarity dataset is a matrix of size N×N wherein N denotes a number of the plurality of 2D images.

In a further implementation form of the first aspect, further comprising: inputting each 2D image into a neural network trained to analyze a target 2D image and output an indication of a target visual feature being depicted within the target 2D image, extracting, for each 2D image, a feature vector from the neural network, wherein the amount of similarity is computed for the feature vectors of each pair.

In a further implementation form of the first aspect, the amount of similarity is computed for the feature vectors of each pair using a cosine similarity.

In a further implementation form of the first aspect, the feature vector is selected from the group consisting of: embeddings obtained from hidden layers of the neural network, an output of an autoencoder implementation of the neural network, and the feature vector is an output of the neural network.

In a further implementation form of the first aspect, further comprising selecting the neural network from a plurality of neural networks each trained to output an indication of a different visual feature, according to the visual feature, wherein the user is viewing the 3D medical image to search for the visual feature.

In a further implementation form of the first aspect, a first subset of the plurality of slabs having fewer than a first threshold number of slabs are designated as small slabs, and a second subset of the plurality of slabs having more than a second threshold number of slabs are designated as large slabs, wherein monitoring comprises monitoring the amount of time corresponding to each small slab and each large slab, and wherein the amount of time spent viewing the certain portion of the 3D medical image being less than the computed minimal amount of viewing time of a certain slab corresponding to the certain portion comprises the amount of time spent viewing a certain small slab is less than a viewing threshold computed based on the amount of time spent viewing a certain large slab.

In a further implementation form of the first aspect, the viewing threshold is selected from a group consisting of: a statistical average and distribution of time spent viewing each 2D images of the large slabs and the time viewing time of the certain small slab comprises the average viewing time of each 2D image of the small slabs, and a ratio between viewing time per 2D image of the large slab and viewing time per 2D image of the small slab.

In a further implementation form of the first aspect, the plurality of slabs are computed by inputting the sequential 2D images into a video scene analysis process that divides a video into scenes of frames, the 2D images corresponding to frames of the video and the scenes corresponding to slabs.

In a further implementation form of the first aspect, the minimal amount of viewing time the user is predicted to spend viewing the respective slab is computed based on an analysis of historical data including monitored amount of time the user and/or other users spent viewing sample 2D images of a plurality of sample 3D images of a plurality of subjects.

In a further implementation form of the first aspect, the minimal amount of time the user is predicted to spend viewing the respective slab is an outcome of a time classifier that receives the slab as input, wherein the time classifier trained on a training dataset of the plurality of 2D images of the plurality of sample 3D images of the plurality of subjects labeled with amount of time spent viewing each 2D images presented on a display.

In a further implementation form of the first aspect, the minimal amount of viewing time for a respective slab is computed based on a number of 2D images included in the respective slab, wherein the minimal amount of time is inversely related to the number of 2D images.

In a further implementation form of the first aspect, the 3D medical image is presented on a display within a graphical user interface (GUI) of a medical image viewing application, and the 2D images of the certain slab are presented within the GUI in response to the amount of time spent viewing a certain portion of the 3D medical image being less than the computed minimal amount of viewing time of the certain slab corresponding to the certain portion.

In a further implementation form of the first aspect, the generating instructions is selected from a group consisting of: presenting the 2D images of the certain slab on the display for an additional view by the user, generating a sound signal played by a microphone, generating a visual signal presented on a display, generating a haptic signal implemented on a haptic device, and adding the 2D images of the certain slab to a second viewing list and presenting an indication of the second viewing list on the display.

In a further implementation form of the first aspect, the 3D medical images are divided into a sequence of a plurality 2D images according to a slice orientation and/or a slice thickness defined by the user viewing the plurality of 2D images and corresponds to the slice orientation and/or slice thickness when the user views the plurality of 2D images.

In a further implementation form of the second aspect, further comprising: in response to the 2D medical image not representing end of the slab, including the 2D medical image as part of the slab, and performing another iteration by receiving another 2D medical image.

In a further implementation form of the second aspect, the 2D medical image and the sequence of 2D images are captured by an imaging device selected from the group consisting of: colonoscope, endoscope, bronchoscope, and 2D ultrasound.

In a further implementation form of the second aspect, further comprising: inputting the 2D image into a neural network trained to analyze a target 2D image and output an indication of a target visual feature being depicted within the target 2D image, extracting, for the 2D image, a feature vector from the neural network, computing an amount of similarity between the feature vector of the 2D image and feature vectors of previously obtained sequence of 2D images, in response to the amount of similarity being below a threshold, determining that the 2D medical image represents the end of the slab.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
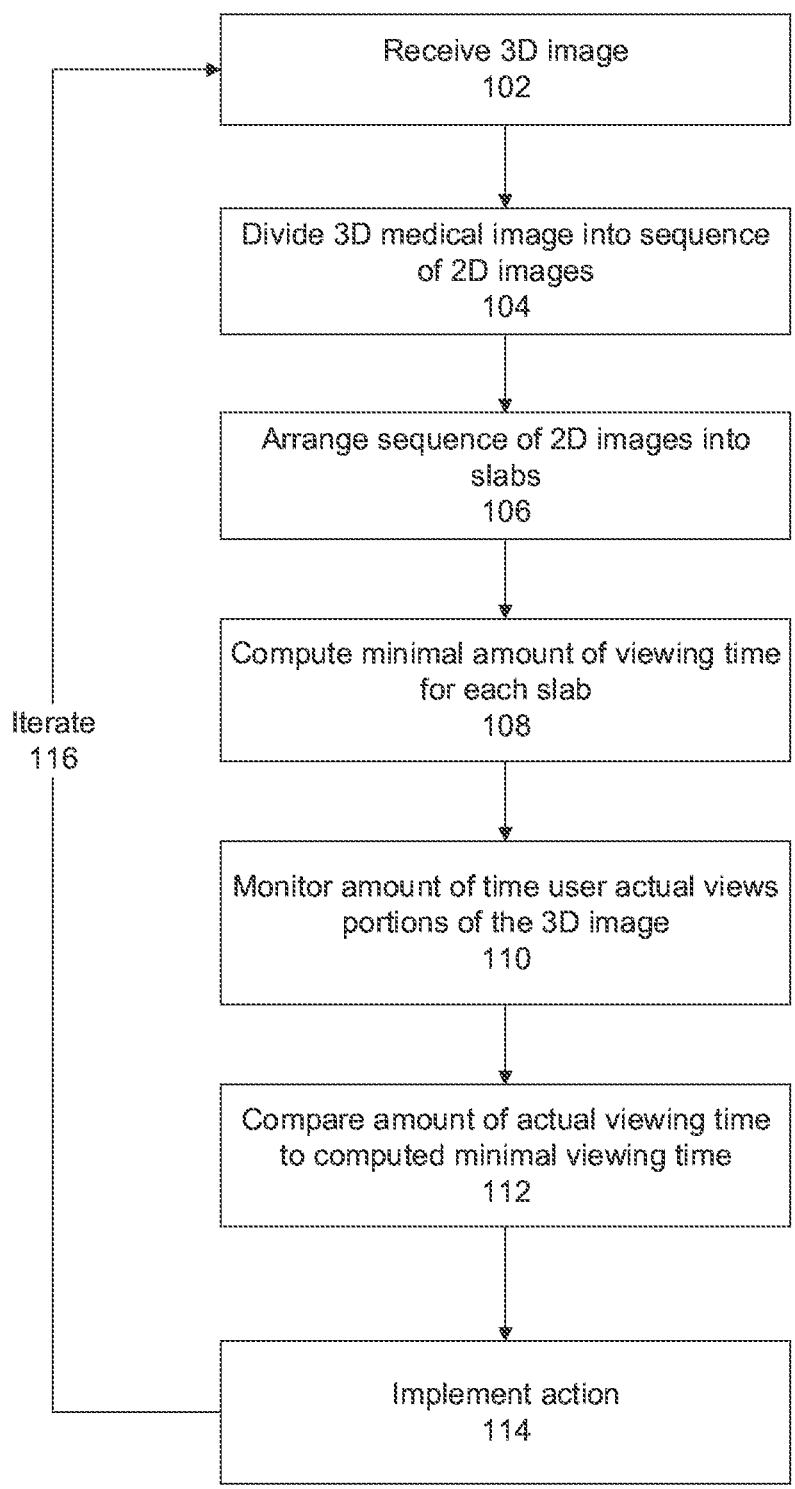
FIG. 1A, is a flowchart of a method for monitoring a user's interaction with a 3D image, to determine whether the user spent more than a computed minimal amount of time viewing certain portions of the 3D image, in accordance with some embodiments of the present invention.

The present invention, in some embodiments thereof, relates to analysis of three dimensional (3D) medical images and, more specifically, but not exclusively, to machine learning methods for monitoring a user's interaction with 3D medical images.

An aspect of some embodiments of the present invention relates to systems, methods, an apparatus, and/or code instructions (i.e., stored on a memory and executable by at least one hardware processor) for monitoring a user's interaction with 3D medical image (e.g., radiologist reading a CT scan, MRI scan, and/or PET scan) and/or with sequential 2D medical images which may be real time images and/or viewed off line, sometimes referred to herein as frames (e.g., obtained during a colonoscopy, bronchoscopy, 2D ultrasound), for detecting an amount of time spent viewing a certain portion of the 3D medical image and/or the sequence of real time 2D images such as a real time video (also referred to herein as a slab) that is less than a computed minimal amount of time that is predicted and/or estimated as required for viewing the respective slab. Detecting slabs for which the user has not spent enough time viewing them may prompt the user to re-review those slabs, which may prevent or reduce likelihood of missing clinically important findings in those slabs, which would otherwise be missed due to the limited amount of time spent. Optionally, the clinically significant findings are expected to be found in a small number of sequential slices, which may be part of a single small slab, or a small number of small slabs (i.e., each slab has a small number of slices, for example, 3-10, 5-15, 1-3 1-20, or other number of slices of a 3D image, and/or 10-100, or 50-500, or 100-300 sequential 2D images which are frames of a 2D video which forms the real time 2D images). For example, 3-5 CT slices of a CT scan that depict a lung nodule being evaluated for lung cancer, and/or 20-100 video frames of a colonoscopy video that depict a small colon polyp. The user is predicted to require spending sufficiently longer time analyzing that slab to determine whether clinically significant findings (e.g., lung nodules, colon polyp) are present or not, in comparison to other slices which may include normal tissue (e.g., normal lung tissue) where the user is predicted to spend sufficiently less time by quickly scanning the normal tissue.

For the case of 3D images, the 3D medical image is divided into a sequence of 2D images (sometimes referred to herein as slices). The sequence of 2D images are arranged (e.g., grouped) into slabs. Each slab includes one or more 2D images. For each slab, a minimal amount of time that the user is predicted to spent viewing the respective slab is computed. While the 3D medical image is being presented on a display, the amount of time that the user actually spent viewing portions of the 3D medical image corresponding to each of the slabs is monitored. In response to the amount of time spent viewing a certain portion(s) of the 3D medical image being less than the computed minimal amount of viewing time of a certain slab(s) corresponding to the certain portion, one or more actions are taken. Exemplary actions include generating instructions for implementation by a user interface indicative of the amount of time spent being less than the computed minimal amount of time, for example, presenting the 2D images of the certain slab on the display for additional viewing, and/or generating alerts to the user.

Optionally, the sequence of 2D images of the 3D images are arranged into slabs by computing a similarity dataset indicative of an amount of similarity between each pair of the 2D images. The amount of similarity may be computed by inputting each 2D image into a neural network trained to analyze a target 2D image and output an indication of a target visual feature being depicted within the target 2D image. For each 2D image, a feature vector is extracted from the neural network, for example, embeddings (e.g., weights of the neurons) of one or more hidden layers of the neural network and/or output of an encoder implementation of the neural network. The amount of similarity is computed for the feature vectors of each pair, for example, using a cosine similarity computed for each pair. The similarity dataset is segmented into multiple groups by minimizing the amount of similarity between consecutive groups and maximizing the amount of similarity within each group. 2D images included within each group are more similar to each other than to other 2D images of other groups. Each group corresponds to one slab.

For the case of real time sequential 2D images, each newly currently captured frame (i.e., 2D image) is analyzed to determine whether the current frame is part of the current slab, or whether the current frame forms a new slab. Once the complete slab has been identified, the minimal amount of viewing time that should have been spent viewing the slab is computed, and compared to the actual amount of time spent viewing that slab. It is noted that in the case of streaming videos, where the number of frames per second is fixed, the amount of estimated time per slab may represent the amount of time spent viewing images of a certain anatomical region. For example, after the colonoscope has been moved to another region in the colon, the estimated time that should have been spent in the previous region is computed based on the time that should have been spent viewing the previous slice corresponding to the previous anatomical region. The actual amount of time spent viewing images of the previous anatomical region may be represented by the actual number of frames captured at that previous anatomical region, which represent the number of frames of the slab. When not enough frames have been captured at the previous anatomical region (represented by the previous slab), indicated by the total time spent viewing frames from the previous anatomical region (represented by frames of the previous slab) being less than the computed minimal amount of time to spend viewing images of the previous region (represented by time spent viewing frame of the previous slab), actions as described herein may be implemented, for example, the user is instructed to return to the previous anatomical location for additional imaging.

At least some implementations of the methods, systems, apparatus, and/or code instructions described herein address the technical problem, which may be a medical problem, of missing important visual findings during reading of 3D medical images. For example, a radiologist scanning an abdominal CT scan may miss a small tumor located in the liver. Radiologists manually scan 3D medical images one 2D slice at a time, until the entire 3D medical image is covered. Manual analysis of 3D medical images, such as Digital Breast Tomosynthesis (DBT), CT, and MRI, requires much more time than analyzing 2D images, since there is much data to process. For example, a chest and abdomen CT scan may include hundreds of 2D slices, each of which require manual reading by the radiologist. However, using 3D data has advantages over 2D data, so using only 2D data is not relevant. For example, the 3D data improves the diagnostic abilities, since visual findings may be traced along multiple sequential 2D slices, for example, aortic aneurysms appear on multiple sequential slices. Since time is limited, and the radiologist is required to browse though many 2D slices during the limited available time, the radiologist may miss some 2D slices, or not spend sufficient time on some 2D slices, potentially missing clinically significant visual findings.

At least some implementations of the methods, systems, apparatus, and/or code instructions described herein address the technical problem, which may be a medical problem, of missing important visual findings during reading of sequential 2D images, which may be real time images (and/or images viewed offline), obtained during an imaging procedure session, for example, colonoscopy, bronchoscopy, endoscopy, and 2D ultrasound imaging. For example, a gastroenterologist scanning real time 2D images of the colon during a colonoscopy may miss a small polyp located in the colon. Gastroenterologists manually scan 2D medical images one 2D image at a time, until the entire anatomical region, for example, the colon, has been visually inspected. Since small visual features such as small polyps appear in a small number of the 2D images, such visual features may be missed.

At least some implementations of the methods, systems, apparatus, and/or code instructions described herein improve the technological field of users interacting with 3D medical images, and/or 2D medical images which may be acquired in real time (and/or viewed offline). In some embodiments, the improvement is at least in the monitoring of the user's interaction with the 3D medical images and/or sequence of 2D images to identify slabs of 2D images for which the user spent less actual time viewing than an amount of predicted time for viewing that slab. A message indicating the identified slabs that require additional viewing time may be presented to the user, and/or the identified slabs may be presented on the display for additional viewing time.

At least some implementations of the methods, systems, apparatus, and/or code instructions described herein improve the technological field of user interfaces, optionally graphical user interfaces (GUI) for viewing 3D medical images and/or 2D medical images which may be acquired in real time (and/or viewed offline). In some embodiments, the improvement is at least in the ability of the GUI to identify slabs of 2D images of a 3D image and/or of the sequence of real time 2D images viewed in the GUI for which the user spent less actual time viewing than an amount of predicted time for viewing that slab. A message indicating the identified slabs that require additional viewing time may be presented to the user in the GUI, and/or the identified slabs may be presented on the display within the GUI for additional viewing time.

At least some implementations of the methods, systems, apparatus, and/or code instructions described herein provide a different approach over other known approaches. For example, some approaches are based on changing the way the 3D image is sliced into 2D images and/or changing the way the 3D image is presented, which restricts the freedom of the radiologist to select the slice orientation and/or to use standard 2D slice viewing approaches. At least some implementations of the methods, systems, apparatus, and/or code instructions described herein enable the user to select the slice orientation and/or to use standard 2D viewing slice approaches. Moreover, none of the known approaches perform the features of comparing the amount of time that the user actually spent viewing slabs of 2D images of the 3D image with a predicted amount of time, to identify slabs where the user did not spend enough time viewing. Such features are performed by at least some embodiments, as described herein.

At least some implementations of the methods, systems, apparatus, and/or code instructions described herein address the above mentioned technical problem, and/or improve the above mentioned technology, by dividing the 3D image and/or the sequence of real time 2D images, into sequential 2D images (also referred to herein as slices), which are arranged into slabs. In the case of 2D real time images, the each newly captured 2D image is analyzed to determine whether the currently captured 2D image is part of the current slab or is part of a new slab. Each slab includes one or more sequential slices. The slices of the slab are more similar to each other, than to other slices of other slabs. Different approaches for arranging the slices into slabs are described herein. For each slab, a minimal viewing time that the user should spend viewing that slab is computed. The interaction of the user with the 3D image and/or real time 2D images is monitored, to determine whether the actual amount of time that the user spent viewing each slab is less than the computed minimal amount of time. When one or more slabs are identified for which the user did not spend enough time, action may be implemented, for example, an alert is generated, and/or the images of the slab are presented for further review.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
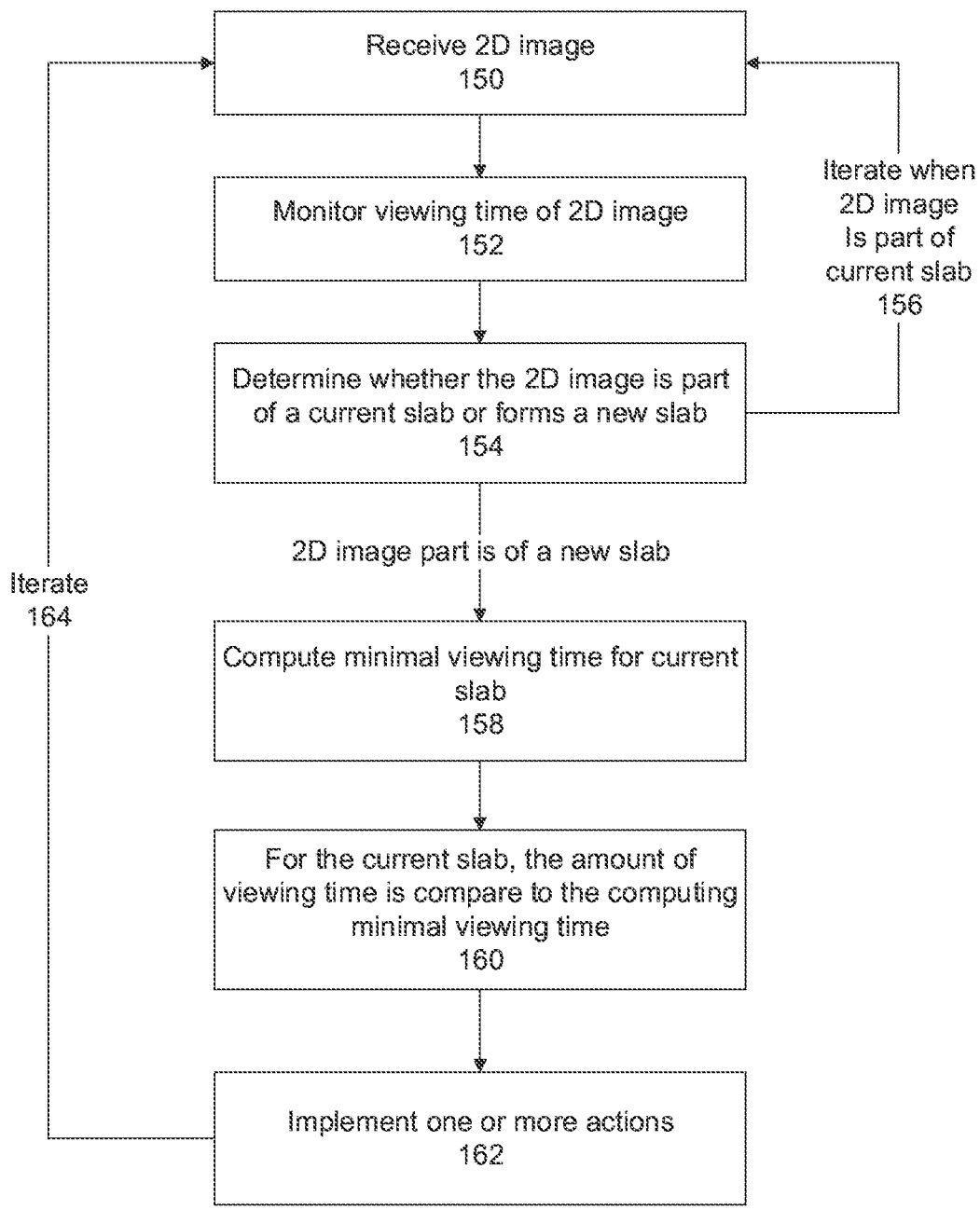
FIG. 1B is a flowchart of a method for monitoring a user's interaction with a sequence of 2D images acquired in real time, to determine whether the user spent more than a computed minimal amount of time viewing certain portions of the sequence, in accordance with some embodiments of the present invention.
Figure 2:
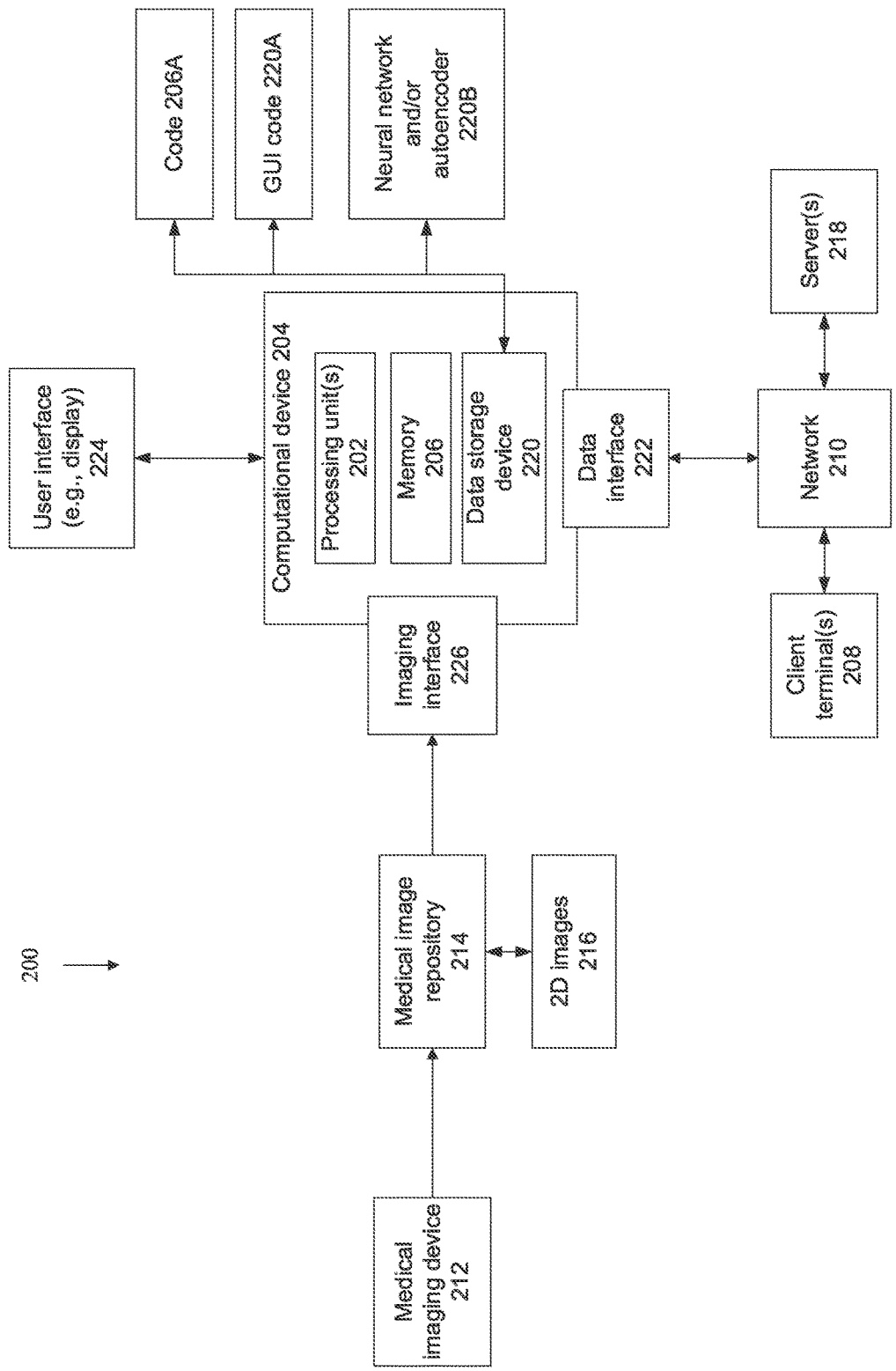
FIG. 2 is a block diagram of components of a system for monitoring the user's interactions with the 3D images and/or the sequence of 2D images acquired in real time, in accordance with some embodiments of the present invention.

Reference is now made to FIG. 1A, which is a flowchart of a method for monitoring a user's interaction with a 3D image, to determine whether the user spent more than a computed minimal amount of time viewing certain portions of the 3D image, in accordance with some embodiments of the present invention. Reference is also made to FIG. 1B, which is a flowchart of a method for monitoring a user's interaction with a sequence of 2D images acquired in real time, to determine whether the user spent more than a computed minimal amount of time viewing certain portions of the sequence, in accordance with some embodiments of the present invention. Reference is also made to FIG. 2, which is a block diagram of components of a system 200 for monitoring the user's interactions with the 3D images and/or the sequence of 2D images acquired in real time, in accordance with some embodiments of the present invention. System 200 may implement the features of the method described with reference to FIG. 1A-1B, by one or more hardware processors 202 of a computing device 204 executing code instructions stored in a memory (also referred to as a program store) 206.

Computing device 204 may be implemented as, for example, a client terminal, a server, a radiology workstation, a virtual machine, a virtual server, a computing cloud, a mobile device, a desktop computer, a thin client, a Smartphone, a Tablet computer, a laptop computer, a wearable computer, glasses computer, and a watch computer.

Computing 204 may include an advanced visualization workstation that sometimes is add-on to a radiology workstation and/or other devices.

Computing device 204 and/or client terminals 208 and/or servers 218 may be implemented as, for example, radiology workstations, image viewing stations, picture archiving and communication system (PACS) server, and electronic medical record (EMR) server.

Multiple architectures of system 200 based on computing device 204 may be implemented. In an exemplary implementation, computing device 204 storing code 206A may be implemented as one or more servers (e.g., network server, web server, a computing cloud, a virtual server) that provides services (e.g., one or more of the acts described with reference to FIG. 1) to one or more servers 218 and/or client terminals 208 over a network 210, for example, providing software as a service (SaaS) to the servers 218 and/or client terminal(s) 208, providing software services accessible using a software interface (e.g., application programming interface (API), software development king (SDK)), providing an application for local download to the servers 218 and/or client terminal(s) 208, and/or providing functions using a remote access session to the servers 218 and/or client terminal(s) 208, such as through a web browser and/or viewing application. For example, users use client terminals 208 to access computing device 204 acting as a PACS server or other medical image storage server. The 3D medical image is presented on a display of client terminal 208. The interaction of the user with the presented 3D and/or 2D frames may be monitored to determine whether viewing time of slabs is above the predicted viewing time, as described herein. The monitoring may be performed locally at the client terminal 208, for example, using an installed application, for example, by the GUI presenting the 3D and/or 2D real time frames, and/or a plug-in and/or screen analysis application. Other features may be performed centrally by computing device 204 and/or locally at client terminal 208. In another implementation, computing device 204 may include locally stored software (e.g., code 206A) that performs one or more of the acts described with reference to FIG. 1A-1B, for example, as a self-contained client terminal and/or server. The 3D image and/or 2D frames may be presented on a display of computing device 204. The monitoring may be performed by code 206A executing on computing device. In yet another implementation, server 218 is implemented as the medical image storage server. Users use client terminals 208 to access the 3D image and/or 2D frames from server 218. The 3D image and/or 2D frames are presented on the display of client terminals 208. Computing device 204 provides enhanced features to the image server, for monitoring the interaction of the user viewing the 3D image to determine whether viewing time of slabs is above the predicted viewing time, as described herein. For example, PACS communicates with computing device using an API for transferring data.

Computing device 204 receives 3D medical images and/or 2D images (e.g., obtained in real time) captured by a medical imaging device(s) 212. The medical imaging device 212 may capture 3D images, for example, CT, MRI, breast tomography, 3D ultrasound, and/or nuclear images such as PET. Alternatively or additionally, the medical imaging device 212 may capture 2D images, optionally in real time, for example, colonoscope, bronchoscope, endoscope, and 2D ultrasound.

Medical images captured by anatomical imaging device 212 may be stored in an anatomical image repository 214, for example, a storage server, a computing cloud, a virtual memory, and a hard disk. The 2D slices 216 which are created by dividing 3D image, and/or the computed slabs of 2D slices and/or 2D frames captured in real time, as described herein, may be stored in medical image repository 214, and/or in other locations such as memory 206 and/or data storage device 220 of computing device 204, on another server 218.

Computing device 204 may receive the 3D image and/or 2D frames, and/or sequence(s) of 2D anatomical image(s) via one or more imaging interfaces 226, for example, a wire connection (e.g., physical port), a wireless connection (e.g., antenna), a network interface card, other physical interface implementations, and/or virtual interfaces (e.g., software interface, application programming interface (API), software development kit (SDK), virtual network connection).

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may code 206A that execute one or more acts of the method described with reference to FIGS. 1A and/or 1B.

Computing device 204 may include data storage device 220 for storing data, for example, GUI code 220A (which may present the 3D images and/or real time frames and monitor viewing time, as described herein) and/or a neural network and/or encoder 220B from which encodings are extracted for determining the slabs, as described herein. Data storage device 220 may be implemented as, for example, a memory, a local hard-drive, a removable storage unit, an optical disk, a storage device, a virtual memory and/or as a remote server 218 and/or computing cloud (e.g., accessed over network 210). It is noted that GUI 220A and/or neural network and/or autoencoder 220B may be stored in data storage device 220, for example, with executing portions loaded into memory 206 for execution by processor(s) 202.

Computing device 204 may include data interface 222, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Computing device 204 may connect using network 210 (or another communication channel, such as through a direct link (e.g., cable, wireless) and/or indirect link (e.g., via an intermediary computing unit such as a server, and/or via a storage device) with one or more of:

Client terminal(s) 208, for example, users using client terminals 208 to access computing device 204 for viewing 3D images and/or 2D frames stored on the server (e.g., computing device 204 acts as the PACS server) may be monitored to determine whether viewing time of slabs is above the predicted viewing time, as described herein.

Server 218, for example, when server 218 is implemented as the PACS server, where users use client terminals 208 to access the PACS server. Computing device 204 provides enhanced features to the PACS server, for monitoring the interaction of the user with the 3D image and/or 2D real time frames to determine whether viewing time of slabs is above the predicted viewing time, as described herein. For example, PACS communicates with computing device using an API.

Medical image repository 214 that stores captured 3D images.

Computing device 204 and/or client terminal(s) 208 and/or server(s) 218 include and/or are in communication with one or more physical user interfaces 224 that include a display for presenting the 3D image and/or real time frames, and/or a mechanism for interacting with the 3D image such as scrolling through 2D slices of the 3D image. Exemplary user interfaces 208 include, for example, one or more of, a touchscreen, a display, a keyboard, a mouse, and voice activated software using speakers and microphone.

Referring now back to FIG. 1A, at 102, a 3D medical image is received, for example, from the imaging device, from a PACS server, and/or from a data storage device.

The 3D medical image may depict one or more regions of the body, for example, full body scan, chest, abdomen, chest plus abdomen, head, and limbs.

The 3D medical image may be an anatomical image depicting anatomical structures within the body (e.g., organs), and/or a functional image depicting functional features within the body (e.g., nuclear scan, functional MRI).

Exemplary imaging modalities that generated 3D medical images include: CT, MRI, fMRI, breast tomography, 3D ultrasound, 3D nuclear imaging, and PET.

At 104, the 3D medical image is divided into a sequence of 2D images (sometimes referred to herein as slices). For example, a 3D CT image is divided into axial slices. Other slice angles may be used, for example, coronal slices, sagittal slices, and/or other angles.

Optionally, the 3D medical images are divided into the sequence of 2D images according to a slice orientation and/or a slice thickness and/or overlap of slices. The slice orientation and/or slice thickness may set according to the user and/or other users and/or standard radiology practice, for example, a history of the slice orientation and/or slice thickness that the user and/or other users previously selected for a similar 3D image (e.g., similar imaging modality and/or similar body part) and/or standard radiology practice for setting the slice orientation and/or slice thickness (e.g., according to imaging modality and/or body part). In other examples, the slice orientation and/or slice thickness may be set based on one or more of: system default value, manual selection by the user, based on the input into the neural network and/or encoder described herein, and/or automatic selection by code (e.g., to optimize the process described herein).

Optionally, the 3D medical image is pre-divided into the sequence of 2D images. For example, CT scans may already be stored and/or defined (e.g., by metadata) in terms of slice. The defined slices may be used.

At 106, the sequence of 2D images are arranged into slabs. Each slab includes one or more 2D images.

The arrangement of the sequence of 2D images into slabs may be performed, for example, using one or more of the following exemplary approaches:

In one exemplary approach, a similarity dataset indicative of an amount of similarity between each pair of the 2D images is computed. The pair of 2D images are neighboring sequential images. For example, for sequential images S1, S2, S3, S4, S5, S6 the pairs are S1-S2, S2-S3, S3-S4, S4-S5, and S5-S5, or in another example, the pairs are S1-S2, S3-S4, and S5-S6. Optionally, the similarity dataset is implemented as a matrix of size N×N where N denotes a number of the 2D images. The similarity dataset is segmented into groups by minimizing the amount of similarity between consecutive groups and maximizing the amount of similarity within each group, where the slabs correspond to the groups. The 2D images included within each group are more similar to one another than to other 2D images of other groups. Segmentation may be performed, for example, using dynamic programming approaches, iterative trial and error (e.g., iteratively moving 2D images on the boundary between one group and the adjacent group), and/or clustering approaches, where each cluster represents a respective group with the added requirement that the images remain sequential.

The amount of similarity of the similarity dataset may be computed by the following exemplary process. Each 2D image is inputted into a neural network. The neural network may be trained to analyze a target 2D image and generate an outcome (i.e., output) of an indication of a target visual feature being depicted within the target 2D image. For example, the neural network may be trained to perform the same function the radiologist is performing, for example, to find nodules in lungs, and/or metastatic cancer in the body, and/or visual features indicative of appendicitis, and/or diverticulitis and/or kidney cancer and/or calcification in arteries. Alternatively, the neural network is trained to perform other functions, that the radiologist is not necessarily performing, for example, segmentation of the liver. The neural network may be selected from multiple neural networks each trained to output an indication of different respective visual features, which may be in different parts of the body. Alternatively, a single neural network is trained to output the multiple different respective features. The neural network may be selected manually and/or automatically, for example, according to the visual feature of the neural network (e.g., the user is viewing the 3D medical image to search for the visual feature), according to the images that the neural network is trained to process (e.g., CT scan, MRI, 3D US) that correspond to the input 2D images, and according to the body region that the neural network is trained to process (e.g., head, chest) that corresponds to the body region depicted in the input 2D images. The neural network may be the same neural network used by a radiologist support system that executes automated machine learning tools on the images to help the radiologist identify clinically significant visual findings.

For each 2D image inputted into the neural network, a feature vector is extracted from the neural network. The feature vector may be obtained from embeddings (e.g. values of weights of neurons) obtained from hidden layers of the neural network, and/or an output of an autoencoder implementation of the neural network where the feature vector is an output of the neural network. The autoencoder may be created from the neural network by removing certain layers of the neural network. The amount of similarity is computed for the feature vectors of each pair of 2D images, for example, using a cosine similarity computed for each pair, or other correlation functions that compute a value indicative of correlation between datasets.

In another exemplary approach, the plurality slabs are computed by inputting the sequential 2D images into a video scene analysis process. Each 2D image represents a frame in the video. The video scene analysis process may be a standard video scene analysis program that divides a video into scenes of frames. The scenes computed by the video scene analysis code correspond to the slabs described herein.

At 108, for each respective slab, a minimal amount of viewing time a user is predicted to spend viewing the respective slab is computed.

The minimal amount of viewing time the user is predicted to spend viewing the respective slab may be computed using one or more exemplary approaches. For example:

In one exemplary approach, the minimal amount of viewing time the user is predicted to spend viewing the respective slab is computed based on an analysis of historical data including monitored amount of time the user and/or other users spent viewing sample 2D images of sample 3D images of sample subjects, that may correspond to the 2D images to the current 2D image. For example, when the current 3D image is a CT of the chest, the minimal amount of time is computed based on viewing times of the same user and/or other users in viewing other chest CTs. The minimal amount of time may be set, for example, as the average of the viewing time of other users and/or the same user, and/or a threshold of a certain number of standard deviations from the average, for example, 1 standard deviation above average, and/or the time met by a certain percentage of other users and/or the same user, such as the time spent viewing by 80% of the other users and/or time in 80% of prior viewing session of the same user.

In another exemplary approach, the minimal amount of viewing time the user is predicted to spend viewing the respective slab is computed based on an outcome of a time classifier that receives the slab as input. In another implementation, the time classifier may receive each 2D image of the slab as input, and compute the minimal amount of time for the slab based on a sum of the time for each 2D image of the lab. The time classifier is trained on a training dataset of 2D images and/or slabs of sample 3D images of multiple subjects labeled with the amount of time spent viewing each 2D image and/or each slab presented on a display.

In yet another exemplary approach, the minimal amount of viewing time the user is predicted to spend viewing the respective slab is computed based on a number of 2D images included in the respective slab. The minimal amount of time is inversely related to the number of 2D images. The smaller the slab, the longer the minimal viewing time. The inverse relationship may be defined by a function, which may be computed based on the actual monitoring data of the user viewing the 2D images, and/or historical data of other users and/or the same user viewing other 3D images, and/or a predefined value.

At 110, while the 3D medical image is presented on a display, the amount of time that the user actually spends viewing respective portions of the 3D medical image is monitored. Each respective portion corresponds to a respective slab. For example, as the user scrolls through 2D slices of the 3D image, the amount of time that each 2D slice is displayed on the screen is measured.

The respective portions of the 3D medical image may be mapped to the computed slabs, for example, using a mapping dataset that maps 3D imaging data of the 3D medical image to the slab, for example, each voxel of the 3D image is mapped to a respective slab, and/or each 2D image presented on the screen is mapped to a respective slab. The mapping may be done, for example, when the user views 2D image of the 3D medical image that do not directly correspond to the computed slices, for example, the user is viewing the CT scan using coronal slices rather than axial slices used to compute the images. It is noted that the portions of the 3D medical image may match the slabs, for example, where the user views predefined slices of the 3D imaging data that were also used to create the slabs, for example, pre-sliced axial images of a CT scan.

The amount of time the user actually spent viewing different portions of the 3D medical image may be measured, for example, by code that analyses the screen presenting the 3D image, and/or by code that is a plug-in to the medical imaging viewing program (e.g., GUI), and/or by the GUI presenting the 3D medical image for viewing. The amount of time may be cumulative, for example, if the user spent 5 seconds viewing one 2D image, then viewed other parts of the 3D image, then came back and viewed the same 2D image for another 7 seconds, the amount of time may be the sum of the two other times, i.e., 12 seconds.

At 112, the amount of time spent that the use actually spent viewing a certain portion(s) of the 3D medical image is compared to the computed minimal amount of viewing time of a certain slab(s) corresponding to the certain portion(s).

When the actual amount of time spent is greater than the minimal amount of time, no action is necessarily taken, since the user spent more time that needed.

Alternatively, when the actual amount of time spent is less than the minimal amount of time, it is an indication that the user did not spent enough time reviewing the certain portion(s) of the 3D medical image.

Optionally, a first subset of the slabs having fewer than a first threshold number of slabs are designated as small slabs. A second subset of the slabs having more than a second threshold number of slabs are designated as large slabs. The thresholds may be set manually and/or automatically, for example, based on the body portion being viewed and/or clinical visual features that are looked for. In such as case, the monitoring of the amount of actual viewing time by the user (e.g., as in 108) is determined for each small slab and each large slab. The amount of time spent viewing a certain small slab is compared to a viewing threshold computed based on the amount of time spent viewing a certain large slab, to determine whether the viewing time is below the viewing threshold indicative not enough time spent, or above the viewing threshold indicating sufficient time spent. Examples of the viewing threshold include: a statistical average and/or distribution of time spent viewing each 2D images of the large slabs (e.g., mean plus two standard deviations below the mean) and the time viewing time of the certain small slab comprises the average viewing time of each 2D image of the small slabs, and a ratio between viewing time per 2D image of the large slab and viewing time per 2D image of the small slab.

At 114, one or more courses of action may be implemented when the actual amount of time spent viewing the certain portion(s) is less than the computed minimal amount of time.

Optionally, instructions are generated for implementation by a user interface, to provide an indication that the amount of time spent on the certain portion(s) of the 3D image is less than the computed minimal amount of time that should be spent viewing the certain portion(s). Exemplary instructions include one or more of: presenting the 2D images of the certain slab on the display for an additional view by the user, generating a sound played by a microphone (e.g., audio message saying to review the liver again, and/or review slices 456-461 again), a visual message presented on a display (e.g., text and/or images and/or video), a haptic signal implemented on a haptic device, and adding the 2D images of the certain slab to a second viewing list and presenting an indication of the second viewing list on the display.

Optionally, the 3D medical image is presented on a display within a graphical user interface (GUI) of a medical image viewing application, and the 2D images of the certain slab (for which the user did not spend enough time) are presented within the GUI.

At 116, one or more features described with reference to 102-114 are iterated, for example, for another 3D image.

Referring now back to FIG. 1B, at 150, a 2D medical image captured in real time is received. The 2D image is part of a sequence of 2D images are captured by an imaging device during a real time imaging procedure. The imaging device may be, for example, a colonoscope, an endoscope, a bronchoscope, and a 2D ultrasound device.

The 2D image may be a captured still image, and/or as part of a stream of frames of a video. The captured 2D image of the video may be referred to herein as a frame.

The current 2D image may be part of an existing slab, which includes previously viewed 2D images. Alternatively, the current 2D image is part of a new slab that is different than the previously viewed slab.

Each slab of 2D images may correspond to a different anatomical location within the body of the subject being imaged.

It is noted that the process described with reference to FIG. 1B may be implemented offline, using previously acquired 2D images (i.e., not real time images). In such implementation, the 2D image is not a real time image, but a stored image captured during an imaging session, which is being viewed offline, for example, the user is viewing 2D images recorded during a colonoscopy session.

At 152, an amount of time the user actually spent viewing (portions of) the 2D medical image is monitored. The amount of time the user spent viewing the previously obtained sequence of 2D images corresponding to the slab may be monitored. The total amount of time spent viewing the slab may be computed as the measured viewing time for the 2D images that are members of the slab. In the case of a video, the total time spend may correspond to the total time of the video captured depicting that slab.

The monitoring may be while the 2D medical image and the previously obtained sequence of 2D images of the slab are presented on a display, Additional exemplary details of monitoring the amount of viewing time the user spends viewing the 2D images is described, for example, with reference to 110 of FIG. 1A.

At 154, the current (e.g., currently presented on a display) 2D medical image is analyzed to determine whether the current 2D medical image represents a last image (e.g., end), and/or is an intermediate part of an existing slab including one or more previously obtained sequence of 2D images, or whether the current 2D medical image is a first image of a new slab. It is noted that the current 2D medical image may be determined as representing the last image of an existing slab after one or multiple frames of a new slab have been received and have been determined to represent the new slab. Once a few (e.g., 1-5, or 2-10, or 2-5, or other ranges) of images which are determined to belong to a new slab, the current 2D medical image (which is a previously obtained 2D medical image after the multiple new images of the new slab have been received) may be identified as the last image of the slab.

In the case of a captured video, where different slabs may correspond to different anatomical regions, multiple frames captured of the same anatomical region (e.g., the scope is held in the same location) may be part of the same slab. A new slab may be identified for images captured of another anatomical region (e.g., the scope is moved to the new anatomical location).

The analysis may be performed using the following exemplary process: the 2D image is inputted into a neural network trained to analyze a target 2D image and output an indication of a target visual feature being depicted within the target 2D image. A feature vector for the 2D image is extracted from the neural network. An amount of similarity between the feature vector of the current 2D image and feature vectors of the previously obtained sequence of 2D images (optionally the 2D image just prior to the current 2D image) is computed. Additional detail of computing the amount of similarity is described, for example with reference to 106 of FIG. 1A.

When the amount of similarity is above a threshold, indicating that the current 2D image is similar to the other previous images, the current 2D medical image is part of the current slab, and feature 156 is implemented. Alternatively, when the amount of similarity is below the threshold, indicating that the current 2D image is not similar to the other previous images, the current 2D medical image represents the end of the slab, and feature 158 is implemented.

At 156, in response to the 2D medical image not representing end of the slab, the current 2D medical image is defined as part of the current slab. Another performing iteration is performed, by iterating features 150-154 for another 2D medical image.

At 158, in response to the 2D medical image representing the end of the current slab and/or start of a new slab, a minimal amount of viewing time a user should spend viewing the current slab is computed, for example, as described with reference to 108 of FIG. 1.

At 160, the amount of time spent actually spent viewing the slab is compared to the computed minimal amount of viewing time. When the amount of time spent actually spent viewing the slab is higher than the computed minimal amount of viewing time, no action is necessarily taken. Alternatively, when the amount of time spent actually spent viewing the slab is lower than the computed minimal amount of viewing time, 162 is implemented.

At 162, one or more actions are implemented, for example, instructions on the display are presented indicating to spend additional time viewing additional 2D images captured from an anatomical region of the subject corresponding to the slab for which the user did not spent enough time viewing. For example, a message is presented on a display and/or an audio message is played over speakers, indicating to the user to return to the previous anatomical region for a second review. When the images are obtained in real time, the same image are not necessarily reviewed, but the user may be instructed to return to the anatomical region to capture more images for reviewing, for example, when the user did not spend enough time in a certain part of the colon (e.g., to detect polyps), the instructions presented may be to return to the same location in the color for additional imaging. Alternatively, the user may be instructed to view the captured 2D images, which have been saved in a storage device again offline. Additional exemplary actions are described, for example, with reference to 114 of FIG. 1A.

At 164, one or more features described with reference to 150-162 are iterated, for example, throughout the imaging session and/or imaging procedure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant 3D medical images will be developed and the scope of the term 3D medical image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for monitoring a user's interaction with 3D medical images, comprising:
   receiving a 3D medical image;
   dividing the 3D medical image into a sequence of a plurality 2D images;
   arranging the sequence into a plurality of slabs each including at least one 2D image, wherein the plurality of slabs are computed by inputting the sequential 2D images into a video scene analysis process that divides a video into scenes of frames, the 2D images corresponding to frames of the video and the scenes corresponding to slabs;
   computing, for each respective slab of the plurality of slabs, a minimal amount of viewing time a user is predicted to spend viewing the respective slab;
   monitoring, while the 3D medical image is presented on a display, an amount of time a user actually spent viewing portions of the 3D medical image corresponding to each of the plurality of slabs;
   in response to the amount of time spent viewing a certain portion of the 3D medical image being less than the computed minimal amount of viewing time of a certain slab corresponding to the certain portion, generating instructions for implementation by a user interface indicative of the amount of time spent being less than the computed minimal amount of time.

2. The method of claim 1, wherein arranging comprises:
   computing a similarity dataset indicative of an amount of similarity between each pair of the plurality of 2D images;
   segmenting the similarity dataset into a plurality of groups by minimizing the amount of similarity between consecutive groups and maximizing the amount of similarity within each group,
   wherein the plurality of slabs correspond to the plurality of groups.

3. The method of claim 2, wherein the similarity dataset is a matrix of size N×N wherein N denotes a number of the plurality of 2D images.

4. The method of claim 2, further comprising:
   inputting each 2D image into a neural network trained to analyze a target 2D image and output an indication of a target visual feature being depicted within the target 2D image;
   extracting, for each 2D image, a feature vector from the neural network;
   wherein the amount of similarity is computed for the feature vectors of each pair.

5. The method of claim 4, wherein the amount of similarity is computed for the feature vectors of each pair using a cosine similarity.

6. The method of claim 4, wherein the feature vector is selected from the group consisting of: embeddings obtained from hidden layers of the neural network, an output of an autoencoder implementation of the neural network, and the feature vector is an output of the neural network.

7. The method of claim 6, further comprising selecting the neural network from a plurality of neural networks each trained to output an indication of a different visual feature, according to the visual feature, wherein the user is viewing the 3D medical image to search for the visual feature.

8. The method of claim 1, wherein a first subset of the plurality of slabs having fewer than a first threshold number of slabs are designated as small slabs, and a second subset of the plurality of slabs having more than a second threshold number of slabs are designated as large slabs, wherein monitoring comprises monitoring the amount of time corresponding to each small slab and each large slab, and wherein the amount of time spent viewing the certain portion of the 3D medical image being less than the computed minimal amount of viewing time of a certain slab corresponding to the certain portion comprises the amount of time spent viewing a certain small slab is less than a viewing threshold computed based on the amount of time spent viewing a certain large slab.

9. The method of claim 8, wherein the viewing threshold is selected from a group consisting of: a statistical average and distribution of time spent viewing each 2D images of the large slabs and the time viewing time of the certain small slab comprises the average viewing time of each 2D image of the small slabs, and a ratio between viewing time per 2D image of the large slab and viewing time per 2D image of the small slab.

10. The method of claim 1, wherein the minimal amount of viewing time the user is predicted to spend viewing the respective slab is computed based on an analysis of historical data including monitored amount of time the user and/or other users spent viewing sample 2D images of a plurality of sample 3D images of a plurality of subjects.

11. The method of claim 10, wherein the minimal amount of time the user is predicted to spend viewing the respective slab is an outcome of a time classifier that receives the slab as input, wherein the time classifier trained on a training dataset of the plurality of 2D images of the plurality of sample 3D images of the plurality of subjects labeled with amount of time spent viewing each 2D images presented on a display.

12. The method of claim 1, wherein the minimal amount of viewing time for a respective slab is computed based on a number of 2D images included in the respective slab, wherein the minimal amount of time is inversely related to the number of 2D images.

13. The method of claim 1, wherein the 3D medical image is presented on a display within a graphical user interface (GUI) of a medical image viewing application, and the 2D images of the certain slab are presented within the GUI in response to the amount of time spent viewing a certain portion of the 3D medical image being less than the computed minimal amount of viewing time of the certain slab corresponding to the certain portion.

14. The method of claim 1, wherein the generating instructions is selected from a group consisting of: presenting the 2D images of the certain slab on the display for an additional view by the user, generating a sound signal played by a microphone, generating a visual signal presented on a display, generating a haptic signal implemented on a haptic device, and adding the 2D images of the certain slab to a second viewing list and presenting an indication of the second viewing list on the display.

15. The method of claim 1, wherein the 3D medical images are divided into a sequence of a plurality 2D images according to a slice orientation and/or a slice thickness defined by the user viewing the plurality of 2D images and corresponds to the slice orientation and/or slice thickness when the user views the plurality of 2D images.

16. A computer implemented method for monitoring a user's interaction with real time 2D medical images, comprising:
in a plurality of iterations:
receiving a 2D medical image captured in real time;
analyzing the 2D medical image to determine whether the 2D medical image represents an end of a slab including at least one of a previously obtained sequence of 2D images, wherein the slab is one of a plurality of slabs computed by inputting the sequential 2D images into a video scene analysis process that divides a video into scenes of frames, the 2D images corresponding to frames of the video and the scenes corresponding to plurality of slabs;
computing a minimal amount of viewing time a user should spend viewing the slab;
monitoring, while the 2D medical image and the previously obtained sequence of 2D images are presented on a display, an amount of time a user actually spent viewing portions of the 2D medical image and the previously obtained sequence of 2D images corresponding to the slab;
in response to the amount of time spent actually spent being less than the computed minimal amount of viewing time, presenting instructions on the display to spend additional time viewing additional 2D images captured from an anatomical region of a subject corresponding to the slab.

17. The method of claim 16, further comprising:
in response to the 2D medical image not representing end of the slab, including the 2D medical image as part of the slab, and performing another iteration by receiving another 2D medical image.

18. The method of claim 16, wherein the 2D medical image and the sequence of 2D images are captured by an imaging device selected from the group consisting of: colonoscope, endoscope, bronchoscope, and 2D ultrasound.

19. The method of claim 16, further comprising:
inputting the 2D image into a neural network trained to analyze a target 2D image and output an indication of a target visual feature being depicted within the target 2D image;
extracting, for the 2D image, a feature vector from the neural network;
computing an amount of similarity between the feature vector of the 2D image and feature vectors of previously obtained sequence of 2D images;
in response to the amount of similarity being below a threshold, determining that the 2D medical image represents the end of the slab.

* * * * *